(12) United States Patent
Sasson et al.

(10) Patent No.: US 6,280,775 B1
(45) Date of Patent: Aug. 28, 2001

(54) ANTIMICROBIAL ORAL COMPOSITION AND METHOD OF USE

(76) Inventors: Joseph Alan Sasson, 40 Redwood Rd., Newton, MA (US) 02459; Riccardo Panicucci, 9 Ashton St., Everett, MA (US) 02149

( * ) Notice: Subject to any disclaimer, the term of this patent is extended or adjusted under 35 U.S.C. 154(b) by 0 days.

(21) Appl. No.: 09/575,351

(22) Filed: May 19, 2000

Related U.S. Application Data

(63) Continuation-in-part of application No. 09/327,579, filed on Jun. 9, 1999, now abandoned.

(51) Int. Cl.[7] .......................... A61K 33/40; A61K 33/00; A61K 33/04; A61K 33/14
(52) U.S. Cl. .................. 424/616; 424/613; 424/615; 424/661; 424/665; 424/703; 424/709; 424/722; 514/835; 514/900; 514/901; 514/902; 514/974
(58) Field of Search ................................ 424/613, 615, 424/616, 661, 665, 703, 709, 722; 514/835, 900, 902, 974, 975, 901

(56) References Cited

U.S. PATENT DOCUMENTS

| | | | | |
|---|---|---|---|---|
| 4,296,102 | * | 10/1981 | Laso | 424/615 |
| 4,296,103 | * | 10/1981 | Laso | 424/615 |
| 4,574,084 | * | 3/1986 | Berger | 424/601 |
| 4,891,216 | * | 1/1990 | Kross et al. | 424/661 |
| 4,902,498 | * | 2/1990 | Agricola et al. | 424/52 |
| 5,051,252 | * | 9/1991 | Schultz et al. | 424/70.4 |
| 5,281,392 | * | 1/1994 | Rubinstein | 422/28 |
| 5,306,440 | * | 4/1994 | Ripley et al. | 252/186.33 |
| 5,324,447 | * | 6/1994 | Lam et al. | 252/187.21 |
| 5,709,992 | * | 1/1998 | Rubinstein | 435/2 |
| 5,858,944 | * | 1/1999 | Keenan et al. | 510/233 |

* cited by examiner

*Primary Examiner*—Jose' G. Dees
*Assistant Examiner*—Frank Choi

(57) ABSTRACT

This invention provides a liquid antimicrobial composition that is particularly useful as a mouthwash for treating or reducing the risk of dental disease. The composition is prepared by mixing a first solution comprising a water soluble metal chlorite compound with a second solution comprising sodium persulfate and hydrogen peroxide. The resulting composition, containing chlorine dioxide, is preferably used at the time of preparation by applying the composition to the locus where treatment is desired.

12 Claims, No Drawings

ANTIMICROBIAL ORAL COMPOSITION AND METHOD OF USE

This application is a continuation-in-part of U.S. Ser. No. 09/327,579 filed Jun. 9, 1999.

FIELD OF THE INVENTION

The present invention describes a two-stage system capable of in situ generation of chlorine dioxide ($ClO_2$) in the presence of hydrogen peroxide ($H_2O_2$) for use in a chemical formulation, more specifically an antimicrobial composition suitable for prophylactic and therapeutic use, including the treatment of oral disease. The system is capable of generating sufficient $ClO_2$ so that, when used in the oral cavity, the composition may inhibit plaque formation, inhibit gingival inflammation and periodontal inflammation, reduce dental caries, and control oral malodor.

BACKGROUND OF THE INVENTION

The use of antimicrobial agents to treat and reduce oral and dental disease is well documented in the professional literature. Among the most efficacious such agents is $ClO_2$, a strong oxidizing agent. $ClO_2$ is well documented as a bactericidal, bacteriostatic, fungicidal, fungistatic, viricidal, and viralstatic agent. It is approved by the EPA under Registration Number 9048-3 for both water purification and food preparation and preservation because of this antimicrobial activity.

$ClO_2$ is also effective in treating malodor. It achieves this efficacy by two mechanisms of action. First, $ClO_2$ oxidizes the sulfide bonds of volatile and odoriferous sulfur compounds (specifically hydrogen sulfide and di-methyl mercaptan bonds) that are metabolic byproducts released by certain anaerobic bacteria documented to reside in the oral cavity; and second, its antimicrobial activity lowers the number of such microorganisms that release these volatile sulfur compounds.

However, because of its reactivity, $ClO_2$ is unstable in an aqueous solution and, as such, cannot be stored at room temperature. Furthermore, since $ClO_2$ is a gas, it cannot be stored in liquid form at room temperature. Thus, various references to "stabilized" $ClO_2$ do not refer to gaseous $ClO_2$, but rather to various chlorous acid-liberating compounds. Unfortunately, chlorous acid, even when buffered, will demineralize tooth enamel and lead to even more significant oral health problems.

One such chlorous acid-liberating compound used is sodium chlorite ($NaClO_2$). References to the use of $NaClO_2$ to generate chlorous acid can be found in the following papers: Chepek C W, Reed O K, Ratcliff Pa., Reduction of Bleeding On Probing With Oral Care Products, *Compendium* 1995, 16(2): 188–196; Bolin V, Ratcliff Pa., Germicidal Effect Of Providone Iodide and $ClO_2$ On Dental Pathogens. *J. Dent Res.* 1987, 373. IADR Abstracts; Grootveld M, Silwood C, Lynch E., Ability of oral heathcare products to alleviate oral malodour. *J Dent. Res.* 1997; 289:50. IADR Abstracts.

Compositions for treating oral malodor that employ chlorine-containing compounds are disclosed in U.S. Pat. Nos. 5,772,986 to Richter; 5,738,840 to Kross; 4,552,679 to Schubel, and 4,808,389 to Ratcliff. These references disclose various vehicles for introducing the compositions to the oral cavity, including liquid rinses, toothpastes (either with or without suds), lozenges, and sprays, as disclosed in U.S. Pat. No. 4,837,009 to Ratcliff. The chemical mechanisms for producing compositions containing chlorous acid are varied. Some references, such as Ratcliff '215, describe the generation of chlorous acid at controlled pH levels using phosphate buffers. U.S. Pat. Nos. 4,891,216 to Kross and 4,902,498 to Agricola et al. disclose a two part system that generates chlorous acid by mixing a metal chlorite or other chlorous acid-liberating compound with a protic acid at acidic pH levels. U.S. Pat. No. 5,667,817 to Kross discloses a two-stage system that requires the use of lactic acid and that results in a composition having a very disagreeable taste, making it unsuitable for use in oral heathcare. As a consequence, this product is not commercially available. However, even those products that are commercially available have significant drawbacks due to their complex chemistries, poor shelf life, poor taste, and poor efficacy.

Because chlorous acid will form $ClO_2$ in aqueous media, there will be some $ClO_2$ generated whenever chlorous acid contacts water. However, no known product is able to consistently provide therapeutic levels of $ClO_2$ capable of reliable and efficacious use, much less to do so in the presence of $H_2O_2$. By employing a single-stage system, known products must control the spontaneous reaction that occurs between the metal chlorite and protic acid to form chlorous acid. For this purpose, various buffers must be used to regulate the system's pH below the $pK_a$ of chlorous acid, resulting in a relatively steady-state generation of chlorous acid. But, for these products to have any useful shelf-life, it is necessary that their steady-state $ClO_2$ levels be fairly low. Furthermore, because the reaction is unidirectional, not only is the product's shelf-life determined by the amount of metal chlorite initially present in the system and its pH, but the end-user is unable to determine how much chlorous acid is present at any given time, as the amount of chlorous acid in the system decays over time.

Commercially available, non-chlorous acid-containing products, such as Mentadent® (active ingredients: baking soda and $H_2O_2$) and Listerine® (active ingredients: thymol, eucalyptol, and methyl salicilate) oral rinses achieve plaque inhibition rates of only 15% and 30%, respectively. These levels are well below the therapeutic and prophylactic benchmark of about 50% plaque inhibition achieved by Peridex® oral rinse (active ingredient: chlorhexidine gluconate), which is available only by prescription. However, even though Peridex® is the most-effective, commercially available plaque inhibitor, it has serious drawbacks that limit its applicability. Most significant among these drawbacks is severe staining to hard oral tissues observed even with brief use. In addition to being unsightly, this black staining actually creates an environment for future plaque buildup, necessitating additional follow-up office visits to be removed by abrasion of the tooth surface, which, in turn, increases the teeth's susceptibility to caries.

There is a strong commercial need for a composite formulation that overcomes these problems. First, the ideal oral care composition would be available over-the-counter yet achieve plaque inhibition rates comparable to compositions currently available only by prescription, inhibit gingival inflammation and periodontal inflammation, reduce dental caries, and control oral malodor. Second, the ideal composition should provide equivalent or superior efficacy to known compositions, yet be pleasing to the taste, thereby increasing patient compliance. Third, the ideal composition should have a superior shelf life due to the chemical stability of the component reactants. Fourth, the composition should be easy to use and have a simple chemistry that reacts under normal environmental conditions (i.e., at ambient temperature and pressure and without the need for multiple steps, pressurized containers, etc.). Fifth, the composition once fully constituted should have a pH value that is suitable for oral use and not be harmful to the teeth or oral tissues. Sixth, the ideal composition should have an effervescent quality for increased aeration of the oral tissues to facilitate the reduction of anaerobic bacteria and other microbes. Seventh, the ideal composition should not stain the teeth, provide an environment for future plaque buildup, require additional treatment, or make the teeth more susceptible to caries. Finally, the ideal composition would enable the rapid, reliable, and predictable generation in situ of therapeutic levels of $ClO_2$.

DESCRIPTION OF THE INVENTION

This invention relates to a method of treating or reducing the risk of a microbial infection using a composition made by mixing a solution of a water soluble metal chlorite with a solution of hydrogen peroxide and sodium persulfate. The composition is especially useful as an oral rinse for treating or reducing the risk of those microbial infections associated with dental disease, such as gingivitis, dental caries and oral malodor. The method comprises the steps of:

(a) providing a first solution comprising a water-soluble chlorite compound, said chlorite compound present at a concentration in the range of about 0.1 to 0.5% by weight, and said first solution having an alkaline pH;

(b) providing a second solution comprising sodium persulfate and hydrogen peroxide, said sodium persulfate present at a concentration in the range of about 1.0 to 10% by weight, said hydrogen peroxide present at a concentration in the range of about 0.3 to 1.5% by weight, and said second solution having a pH in the range of about 1 to 6;

(c) mixing the first solution and the second solution together to provide an antimicrobial composition, wherein said composition has a pH below about 7; and applying the composition of step (c) to the locus of the microbial infection.

A preferred water soluble chlorite compound for the first solution is $NaClO_2$. The water soluble chlorite is present at a concentration in the range of about 0.1 to 0.5% by weight, preferably about 0.25 to 0.32%. This first solution is maintained at an alkaline pH above about 7, preferably around pH 8.

The second solution comprising sodium persulfate ($Na_2S_2O_8$) and hydrogen peroxide ($H_2O_2$) is maintained at a pH in the range of about 1 to 6. The sodium persulfate is present at a concentration in the range of about 1.0 to 10% by weight, preferably in the range of about 3 to 5%. The term "hydrogen peroxide" as used herein includes hydrogen peroxide itself as well as any peroxide generator such as urea peroxide, zinc peroxide, calcium peroxide, sodium percarbonate and the like. The hydrogen peroxide is present at a concentration in the range of 0.3 to 1.5% by weight, preferably in the range of about 0.3 to 0.75%.

While this invention is not intended to be limited by any particular theory or mechanism of action, it is believed that the therapeutic effectiveness of the present compositions is due at least in part to the formation of chlorine dioxide ($ClO_2$). When the first and second solutions are mixed, $ClO_2$ is formed by the sodium persulfate oxidation of the water-soluble chlorite compound as described by the reactions shown below. Chlorine dioxide is a known antimicrobial agent. Hydrogen peroxide is also believed to be responsible in part for the therapeutic effectiveness of the present compositions, even though it is known that in the presence of $H_2O_2$, $ClO_2$ is reduced back to $ClO_2^-$ and hydrogen peroxide is consumed.

These reactions are illustrated below:

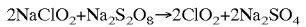

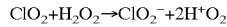

Applicants have found that when there is an adequate amount of sodium persulfate as described herein, relatively small amounts of water soluble metal chlorite and hydrogen peroxide may be used together to provide an effective oral rinse.

The amounts of water soluble metal chlorite compound, hydrogen peroxide and sodium persulfate ingredients described above are based on mixing the first and second solutions in approximately equal volumes. These volumes may be varied to adjust for variations in the concentration of the ingredients in the first and second solutions. Accordingly, another embodiment of the invention relates to a method for treating or reducing the risk of a microbial infection comprising the step of applying an antimicrobial composition having a pH below about 7 to the locus or surface of the microbial infection, wherein said composition is prepared by mixing a first solution with a second solution, the first solution comprising about 0.05 to 0.25% of a water soluble metal chlorite and the second solution comprising about 0.5 to 5% sodium persulfate and about 0.15 to 0.75% hydrogen peroxide, wherein all quantities are based on the weight of the antimicrobial composition.

The antimicrobial composition obtained after mixing the solutions will have $ClO_2$ at a concentration in the range of about 1 to 100 ppm, preferably in the range of about 2 to 20 ppm; hydrogen peroxide in the range of about 0.15 to 0.75%, preferably in the range of about 0.15 to 0.4%; sodium persulfate in the range of about 0.5 to 5%, preferably 1.5 to 2.5%; and $ClO_2^-$ in the range of about 0.05 to 0.5%. Accordingly, another embodiment of this invention relates to a method for treating or reducing the risk of microbial infection comprising the step of applying to the locus of the microbial infection an antimicrobial composition comprising (a) $ClO_2$ at a concentration in the range of about 1 to 100 ppm, preferably in the range of about 2 to 20 ppm; (b) hydrogen peroxide in the range of about 0.15 to 0.75% by weight, preferably in the range of about 0.15 to 0.4%; (c) sodium persulfate in the range of about 0.5 to 5% by weight, preferably 1.5 to 2.5%; and (d) $ClO_2^-$ in the range of about 0.05 to 0.5% by weight, wherein the pH of the composition is below about 7.

For adjusting the pH, any suitable buffer may optionally be used such as a bicarbonate buffer, a citrate buffer or a phosphate buffer. When used, the buffer will typically be present at a concentration in the range of about 0.1 to 1.0% by weight. Bicarbonate is a preferred buffer system. Any suitable food-grade acid or base may be used to prepare the buffer system or to otherwise adjust the pH. Preferred acids are phosphoric acid and citric acid, optionally supplemented by tannic acid, and a preferred base is sodium bicarbonate.

The composition may contain optional ingredients to improve taste, appearance or mouthfeel in order to enhance its appeal to the consumer. Such optional ingredients include colorants, sweeteners, flavorings and surfactants that are known ingredients in commercially available mouthwash. Examples of colorants include FDC Red 40, FDC Green 3, FDC Brown mixture, FDC Yellow 5, DC Red 19, DC Red 33, DC Yellow 10, and the like, which are typically present in about 0.01 to 0.2 weight percent. Examples of suitable sweeteners include glycerin and sugar alcohols like sorbitol or artificial sweeteners such as aspartame, saccharin or acesulfame. Sweetening agents are generally used at levels of from about 0.005% to about 2% by weight of composition. Examples of flavorants include oils of spearmint, peppermint, wintergreen, sassafras, clove, sage, eucalyptus, cinnamon, lemon, orange, and methyl salicylate. Flavorants are used in a quantity of about 0.1 percent by weight. A surfactant can be added as an optional ingredient in a quantity of about 0.2–2 weight percent, and preferably is selected from orally-compatible nonionic and anionic polymers which are commercially available for oral hygiene applications. Nonionic oral surfactants are illustrated by laurate esters of sorbitol consisting of the monoester condensed with about 15–25 moles of ethylene oxide, such as Tween 20 (ICI Americas). Another suitable type of oral surfactants are the polymers of polyoxyethylene and polyoxypropylene, such as Pluronic F-108 (BASF-Wyandotte). Anionic oral surfactants are illustrated by alkyl sulfonates and sulfates, such as sodium lauryl sulfate or a sulfonated monoglyceride of a $C_{10}$–$C_{18}$ fatty acid. The present composition may also contain deodorizing agents, anti-foam agents, ethanol or other alcohols, as well as other conventional ingredients.

It is preferred that the present composition be prepared fresh from the two solutions and used at or near the time of preparation. The composition is best used between about 1 to 5 minutes after it is prepared. However, if the composition is left to sit for several hours, its effectiveness will begin to diminish. In the field of oral mouthwashes, suitable containers have been developed for maintaining separate solutions that are to be mixed at the time of use by the consumer. U.S. Pat. Nos. 5,252,312, 5,289,950 and 5,392,947, incorporated herein by reference, describe such dispensing containers for dental mouthwash. The containers have at least two discreet compartments so that the contents of the compartments may be dispensed simultaneously.

Accordingly, another embodiment of this invention relates to a dental mouthwash product comprising:

(a) a first liquid component comprising a water-soluble chlorite compound, said chlorite compound present at a concentration in the range of about 0.1 to 0.5% by weight, and said first component having an alkaline pH;

(b) a second liquid component comprising a second solution comprising sodium persulfate and hydrogen peroxide, said sodium persulfate present at a concentration in the range of about 1.0 to 10% by weight, said hydrogen peroxide present at a concentration in the range of about 0.3 to 1.5% by weight, and said second component having a pH in the range of about 1 to 6;

(c) a dispensing container which houses a first compartment with an outlet end containing the first liquid component and a second compartment with an outlet end containing the second liquid component;

(d) a closure mechanism for closing the compartments over the outlet ends; and (e) a closure means for allowing the first and second liquid components to be simultaneously dispensed.

Such containers are especially well-suited to simultaneously dispensing equal quantities of the two liquid components. Optionally, the outer walls of one or both of the compartments may be constructed of a translucent or clear material so that the liquid level within the container may be viewed.

The composition may be used as an oral rinse for treating dental disease. Such disease includes gingivitis, dental caries and oral malodor. The amount of composition and the frequency of treatment may be varied depending on the type and severity of the disease and on the mode of application. The amount of composition used per treatment may vary from about 0.1 ml to 100 ml depending on the application. The lower amounts may be sufficient if the composition is to be applied directly, for example, by using a syringe or other means of direct application. For an oral rinse, the amounts typically vary from a few milliliters to about 100 ml per treatment, preferably from about 25 to 50 ml. The composition may be used as a mouthwash daily or multiple times during the day or in accordance with a treatment regimen that would be prescribed by one skilled in the art of dental care. For treating the dental diseases described herein, treatments will generally be made once to a few times per day, preferably twice per day.

The composition may also be used in dental appliance therapy, especially for treating extra-oral appliances such as removable partial dentures, full dentures, night guards, and orthodontic appliances. The appliance is treated by immersing it in the composition for a suitable period of time, usually about 10 to 15 minutes.

The pH of the resulting composition should be below 7, but above the $pK_a$ of chlorous acid. It is known that $ClO_2$ is generated from $NaClO_2$ at pH values below 7 in the absence of $Na_2S_2O_8$. However, the generation is quite slow (on the order of days and months). In the presence of $Na_2S_2O_8$, under the conditions described above, therapeutic levels of $ClO_2$ are believed to be generated in seconds. Increasing the concentration of $Na_2S_2O_8$ by weight will cause a more rapid generation of $ClO_2$. Table 1 shows that for a constant level of $NaClO_2$ the generation of $ClO_2$ increases with increasing levels of $Na_2S_2O_8$. The levels of $ClO_2$ generated by this reaction are within the levels that are expected to inhibit the formation of gingival plaque.

TABLE 1

Generation of $ClO_2$ in 5 minutes after a 1:1 mixture of a $NaClO_2$ solution (0.25%) and a solution of $Na_2S_2O_8$ (ranging from 1–5%) at pH = 5.

| % $NaClO_2$ | % $Na_2S_2O_8$ | $ClO_2$ ppm |
| --- | --- | --- |
| 0.25 | 1 | 2.5 |
| 0.25 | 2 | 5.5 |
| 0.25 | 3 | 10.0 |
| 0.25 | 4 | 12.5 |
| 0.25 | 5 | 17.0 |

Table 2 below shows the effects of $H_2O_2$ on the reaction system. As discussed above, although an oxidant, in this reaction $H_2O_2$ will reduce $ClO_2$ back into $NaClO_2$. In the above stoichiometry, $ClO_2$ is generated even in the presence of $H_2O_2$. While the apparent $ClO_2$ concentration decreases with increasing levels of $H_2O_2$, even at the highest levels of $H_2O_2$ (1.2%), there is sufficient $ClO_2$ to inhibit gingival plaque. For products requiring less $H_2O_2$, either higher levels of $ClO_2$ can be obtained or the levels of $NaClO_2$ and $Na_2S_2O_8$ may be adjusted, in a manner that would be apparent to one skilled in the art, to yield desired levels of $ClO_2$.

TABLE 2

$ClO_2$ generation 5 minutes after a 1:1 mixture of a $NaClO_2$ (0.25%) solution and a solution containing $Na_2S_2O_8$ (5%) and $H_2O_2$ (ranging from 0–1.2%) at pH = 5.

| % $H_2O_2$ | % $NaClO_2$ | % $Na_2S_2O_8$ | $ClO_2$ ppm |
|---|---|---|---|
| 0 | 0.25 | 5 | 17 |
| 0.025 | 0.25 | 5 | 16.5 |
| 0.075 | 0.25 | 5 | 15.6 |
| 0.15 | 0.25 | 5 | 13.5 |
| 0.3 | 0.25 | 5 | 11.3 |
| 0.6 | 0.25 | 5 | 9.0 |
| 1.2 | 0.25 | 5 | 6.0 |

In the case where the application also calls for the use of $NaHCO_3$, such as in bicarbonate- and peroxide-containing products, the pH of the persulfate/peroxide-containing component should be sufficiently acidic such that upon mixing with the $NaClO_2$/bicarbonate-containing component the resulting pH is less than 7.

Table 3 below shows a formula for the two-component system of the present invention. The ranges given below represent the various conditions that could result in levels of $ClO_2$ that inhibit plaque. In general the $ClO_2$ levels will be dependent on the level of $NaClO_2$ in the base and the level of $H_2O_2$ and $Na_2S_2O_8$ in the activator. The level of $NaHCO_3$ in the base will determine the level of phosphoric acid ($H_3PO_4$) that should be used in order to adjust the pH of the activator. Upon mixing the base and activator, the resulting pH should be below 7. Increasing levels of $NaHCO_3$ in the base therefore will require increasing levels of phosphoric acid in the activator to achieve a final pH of less than 7 when the two phases are mixed.

TABLE 3

Formulation for Two-Component System.

| Base (Solution 1) | | Activator (Solution 2) | |
|---|---|---|---|
| Component | Wt. % | Component | Wt. % |
| $NaClO_2$ | 0.1–0.5 | $H_2O_2$ | 0.3–1.5 |
| $NaHCO_3$ | up to 1.0 | $Na_2S_2O_8$ | 1.0–10.0 |
| Surfactant | 0.01–1.0 | Surfactant | 0.01–1.0 |
| Flavor | 0.5–2.0 | Flavor | 0.5–2.0 |
| Ethanol | up to 16.0 | $H_3PO_4$ | as needed |
| Water | balance | Water | balance |

The lower levels of $NaClO_2$ and $Na_2S_2O_8$ can be used to generate the desired levels of $ClO_2$ if the $H_2O_2$ is eliminated from the formulation. The level of $NaHCO_3$ will not effect the generation of $ClO_2$ where no $H_2O_2$ is present. However, the pH of the resulting solution should be below 7 if $NaHCO_3$ is used in the formula. It may be desirable in some applications to include bicarbonate but not $H2O_2$.

EXAMPLE

A standardized Ramfjord protocol was followed for all subjects in the study. Forty three (43) adult subjects, between the ages of 18 and 65, were recruited for a two-cell, 48 hour plaque inhibition study against a water placebo control. The study was conducted in a double blind manner using the formulation described in Table 4 below. The subjects received 50 ml unit doses, two times per day over a 48 hour period. Neither examiner nor subject had knowledge of the test product identity.

TABLE 4

Clinical formula evaluated in a double-blind, two-cell, 48 hour plaque inhibition study against a water placebo control.

| Base | | Activator | |
|---|---|---|---|
| Component | Wt. % | Component | Wt. % |
| $NaClO_2$ | 0.32 | $H_2O_2$ | 0.75 |
| $NaHCO_3$ | 0.5 | $Na_2S_2O_8$ | 5.0 |
| Surfactant | 0.5 | Surfactant | 0.5 |
| Flavor | 0.5 | Flavor | 0.5 |
| Ethanol | 10.0 | $H_3PO_4$ | as needed |
| Water | balance | Water | balance |

On day one the panelists received dental prophylaxis and were instructed to use the assigned rinse. No oral hygiene regimens, besides the rinsing with the test product or placebo, were allowed. At the end of the two-day treatment, panelists received a plaque evaluation of the Ramfjord teeth as well as all other molars, excluding third molars. The plaque were evaluated for supragingival plaque using the Distal Mesial Plaque Index scoring method. The findings are shown in Table 5 below.

TABLE 5

Clinical results obtained in the double-blind, two-cell, 48 hour plaque inhibition study against a water placebo control.

| Tooth Surface | Product | Number of subjects | Mean | Standard Deviation | P Value |
|---|---|---|---|---|---|
| Mouth | Placebo | 22 | 1.13 | 0.27 | 0.0001 |
| | Test Rinse | 21 | 0.63 | 0.12 | |
| MO | Placebo | 22 | 0.59 | 0.26 | 0.0001 |
| | Test Rinse | 21 | 0.23 | 0.12 | |
| MM | Placebo | 22 | 1.01 | 0.28 | 0.0001 |
| | Test Rinse | 21 | 0.46 | 0.22 | |
| MG | Placebo | 22 | 1.29 | 0.33 | 0.0001 |
| | Test Rinse | 21 | 0.75 | 0.20 | |
| FM | Placebo | 22 | 1.45 | 0.44 | 0.0002 |
| | Test Rinse | 21 | 0.96 | 0.31 | |
| FD | Placebo | 22 | 1.70 | 0.44 | 0.0001 |
| | Test Rinse | 21 | 1.06 | 0.20 | |
| DG | Placebo | 22 | 1.72 | 0.42 | 0.0001 |
| | Test Rinse | 21 | 1.00 | 0.22 | |
| DM | Placebo | 22 | 1.36 | 0.46 | 0.0001 |
| | Test Rinse | 21 | 0.63 | 0.32 | |
| DO | Placebo | 22 | 0.53 | 0.37 | 0.0014 |
| | Test Rinse | 21 | 0.21 | 0.23 | |
| R | Placebo | 22 | 0.55 | 0.18 | 0.0001 |
| | Test Rinse | 21 | 0.32 | 0.14 | |

The mean values shown in Table 5 are mean plaque scores for each tooth surface examined on the Ramfjord teeth. The greater the mean value, the greater the relative plaque accumulation. The data show that the $ClO_2$ group mean plaque scores were significantly lower than the water placebo group mean scores for all individual surfaces and for the total mouth. Therefore it can be concluded that the $ClO_2$ rinse is significantly more efficacious than water in the inhibition of dental plaque on the teeth, over a 48 hour period with four applications.

In addition to use within the oral cavity, it is contemplated that the present invention has applicability for use on the vaginal, anal, nasal, and ocular mucous membrane surfaces, topically, and in vitro, as, e.g., as a contact lens wash or dental apparatus wash.

While we have described a number of embodiments of this invention, it is apparent that our basic examples may be altered to provide other embodiments which utilize the compositions and methods of this invention. Therefore, it will be appreciated that the scope of this invention is to be defined by the appended claims rather than by the specific embodiments which have been represented by way of example.

We claim:

1. A method of treating or reducing the risk of a microbial infection comprising the steps of:
   (a) providing a first solution comprising a water-soluble chlorite compound, said chlorite compound present at a concentration in the range of about 0.1 to 0.5% by weight, and said first solution having an alkaline pH;
   (b) providing a second solution comprising sodium persulfate and hydrogen peroxide, said sodium persulfate present at a concentration in the range of about 1.0 to 10% by weight, said hydrogen peroxide present at a concentration in the range of about 0.3 to 1.5% by weight, and said second solution having a pH in the range of about 1 to 6;
   (c) mixing the first solution and the second solution to provide an antimicrobial composition, wherein said composition has a pH below 7; and
   (d) applying the composition of step (c) to the locus of the microbial infection.

2. A method of treating or reducing the risk of dental disease comprising the steps of:
   (a) a first liquid component comprising a water-soluble chlorite compound, said chlorite compound present at a concentration in the range of about 0.1 to 0.5% by weight, and said first component having an alkaline pH;
   (b) a second liquid component comprising a second solution comprising sodium persulfate and hydrogen peroxide, said sodium persulfate present at a concentration in the range of about 1.0 to 10% by weight, said hydrogen peroxide present at a concentration in the range of about 0.3 to 1.5% by weight, and said second component having a pH in the range of about 1 to 6;
   (c) mixing the first solution and the second solution to provide an antimicrobial composition, wherein said composition has a pH below 7; and
   (d) applying the composition of step (c) to the locus of the microbial infection.

3. The method of claim 2, said method having one or more of the following features:
   (a) the water-soluble chlorite compound in the first solution is present at a concentration in the range of about 0.25 to 0.32% by weight;
   (b) the water-soluble chlorite compound is $NaClO_2$;
   (c) the sodium persulfate in the second solution is present at a concentration in the range of about 3 to 5% by weight;
   (d) the hydrogen peroxide in the second solution is present at a concentration in the range of about 0.3 to 0.75% by weight; and/or
   (e) the antimicrobial composition has a pH in the range of 4–7.

4. The method of claim 3 wherein:
   (a) the water-soluble chlorite compound in the first solution is present at a concentration in the range of about 0.25 to 0.32% by weight;
   (b) the water-soluble chlorite compound is $NaClO_2$;
   (c) the sodium persulfate in the second solution is present at a concentration in the range of about 3 to 5% by weight;
   (d) the hydrogen peroxide in the second solution is present at a concentration in the range of about 0.3 to 0.75% by weight; and/or
   (a) the antimicrobial composition has a pH in the range of 4–7.

5. The method of claim 2 wherein the antimicrobial composition further comprises one or more of the following ingredients: a colorant, a sweetener, a flavoring and/or a surfactant.

6. A method of treating or reducing the risk of a microbial infection comprising the step of applying to the locus where treatment or prevention is desired, an antimicrobial composition comprising (a) about 1–100 ppm chlorine dioxide; (b) about 0.5–5% by weight of sodium persulfate; (c) about 0.15–0.75% by weight of hydrogen peroxide; and (d) about 0.05 to 0.5% by weight of a chlorite, said composition having a pH below 7.

7. The method of claim 6 wherein (a) is about 2 to 20 ppm chlorine dioxide; (b) is about 1.5 to 2.5% sodium persulfate; (c) is about 0.15 to 0.4% hydrogen peroxide; (d) the water soluble chlorite compound is $NaClO_2$; and/or (e) the pH of the composition is between about 4–7.

8. The method of claim 7 wherein the antimicrobial composition comprises (a) about 2 to 20 ppm chlorine dioxide; (b) about 1.5 to 2.5% sodium persulfate; (c) about 0.15 to 0.4% hydrogen peroxide; (d) about 0.05 to 0.5% $NaClO_2$; and (e) the pH of the composition is between about 4–7.

9. The method of claim 6 wherein the antimicrobial composition is an oral rinse for treating dental disease.

10. The method of claim 2 or 6 wherein the dental disease is selected from gingival plaque formation, dental caries or oral malodor.

11. A method for treating or reducing the risk of a microbial infection comprising the step of applying an antimicrobial composition having a pH below about 7 to the locus or surface of the microbial infection, wherein said composition is prepared by mixing a first solution with a second solution, the first solution comprising about 0.05 to 0.25% of a water soluble metal chlorite and the second solution comprising about 0.5 to 5% sodium persulfate and about 0.15 to 0.75% hydrogen peroxide, wherein the quantities of chlorite, sodium persulfate and hydrogen peroxide are based on the weight of the antimicrobial composition.

12. A dental mouthwash product comprising:
   (a) a first liquid component comprising a water-soluble chlorite compound, said chlorite compound present at a concentration in the range of about 1.0 to 0.5% by weight, and said second solution having an alkaline pH;
   (b) a second liquid component comprising a second solution comprising sodium persulfate and hydrogen peroxide, said sodium persulfate present at a concentration in the range of about 1.0 to 10% by weight, said hydrogen peroxide present at a concentration in the range of about 0.3 to 1.5% by weight, and said second solution having a pH in the range of about 1 to 6; and
   (c) a suitable container that separately houses the first liquid component and the second liquid component.

* * * * *